United States Patent [19]

Silvis

[11] Patent Number: 5,621,139

[45] Date of Patent: Apr. 15, 1997

[54] PROCESS FOR PREPARING ALKOXYLATED ALKYL GLYCERYL ETHER SULFONATES

[75] Inventor: Salvatore J. Silvis, Lambertville, N.J.

[73] Assignee: Colgate-Palmolive Company, New York, N.Y.

[21] Appl. No.: 324,953

[22] Filed: Oct. 18, 1994

[51] Int. Cl.⁶ .................................. C07C 309/00
[52] U.S. Cl. .................................................. 562/111
[58] Field of Search .................................... 562/111

[56] References Cited

U.S. PATENT DOCUMENTS

| | | | |
|---|---|---|---|
| 2,989,547 | 6/1961 | Whyte et al. | 549/555 |
| 3,024,273 | 3/1962 | Whyte et al. | 562/103 |
| 3,228,979 | 1/1966 | Gaertner | 562/42 |
| 4,502,538 | 3/1985 | Wellington et al. | 166/252 |
| 5,310,508 | 5/1994 | Subramanyam et al. | 252/549 |

FOREIGN PATENT DOCUMENTS

| | | |
|---|---|---|
| 0156601 | 10/1985 | European Pat. Off. . |
| 2282809 | 4/1995 | United Kingdom . |

OTHER PUBLICATIONS

Whyte, Alkyl Glyceryl Ether Sulfonates, Surfactant Science Series, vol. 7, Anionic Surfactants, part 2, pp. 483–494.

*Primary Examiner*—Joseph Conrad
*Attorney, Agent, or Firm*—Martin Barancik

[57] ABSTRACT

A continuous process for preparing alkoxylated alkyl glyceryl ether sulfonates which comprises reacting in the presence of water a mixture of an alkali metal sulfide and bisulfite with a mixture of alkoxylated glycidyl ethers comprising a major quantity of a

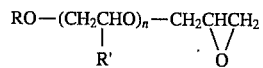 Formula 1 wherein R is alkyl or alkenyl of about eight to twenty carbon atoms, R' is H or methyl, n is an average integer value of 1 to about 12 to obtain alkoxylated sulfonated product having as a major quantity of the alkoxylated product

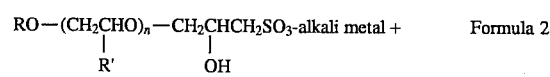 Formula 2 at an elevated temperatures of at least 125° C., a pressure sufficient to maintain the reaction mass liquid at the reaction temperature and at least 20 wt % of the reaction mass as sulfonated product.

18 Claims, 1 Drawing Sheet

PROCESS FOR PREPARING ALKOXYLATED ALKYL GLYCERYL ETHER SULFONATES

BACKGROUND OF THE INVENTION

Alkyl glyceryl ether sulfonates (AGES) are well known as detergents utilized in personal care cleansing products. Although much literature is present disclosing their use in compositions, there is not a substantial amount of published literature relating to their synthesis. For example a 1976 review article by David Whyte entitled Alkyl Glyceryl Ethers Sulfonates appearing in Surfactant Science Series, Vol. 7, Anionic Surfactants part 2 at pages 483–494 reviews methods of preparing AGES. However most of the citations reviewed are significantly older than the review article. Among the reviewed documents are two Whyte U.S. patents, U.S. Pat. Nos. 2,989,547 and 3,024,273. In these patents, several methods of making AGES are disclosed including a detailed continuous process complete with figures in U.S. Pat. No. 3,024,273. This patent discloses the conversion of the chlorohydrin to the alkyl glyceryl ether sulfonate by the Strecker reaction using sodium sulfite.

The recycled sulfonate product is used to promote emulsification of the reactants in the mixer so that the sulfonation reaction is readily maintained and the recycled sulfonate normally comprises about 5% by weight of the total amount of material fed into the system. Depending upon the concentration of sodium sulfite, the undried sulfonation product will contain at least 50% water. Reaction contact time is from 4 to 20 minutes but reactant flow and reactor size are normally scaled so that reactor residence time is about ten minutes.

In U.S. Pat. No. 2,989,547 the glycidyl ether intermediate is disclosed as sulfonated to the alkyl glyceryl ether sulfonate using a mixture of sodium sulfite and bisulfite. The process can be carried out in a continuous manner. This sulfonation reaction can be carried out at moisture levels of well below 50% and even as low as about 30%. Using a 10% "paste seed" of alkyl glyceryl ether sulfonate, the batch reaction will initially proceed at temperatures as low as 300° F.

With respect to these disclosures in the above two U.S. patents, several cautionary statements are made in the aforementioned Whyte review article. For example at page 490, Whyte states that solids contents of greater than 60% can be achieved in glycidyl ether sulfonation but difficulties in temperature control and excessive product viscosities make it undesirable to achieve these higher solids levels.

Methods of making alkoxylated alkyl glyceryl ether sulfonates are disclosed in Wellington et al, U.S. Pat. No. 4,502,538 and Gaertner U.S. Pat. No. 3,228,979. In Wellington, the corresponding glycidyl ether (epoxide) is converted to the sulfonate by reacting with aqueous sodium bisulfite or first reacting it with sodium hydroxide and then reacting it with the bisulfite. No temperatures are mentioned. Gaertner states than an alkali metal sulfite or bisulfite can be used to sulfonate the corresponding ether while preferably neutralizing the hydroxide as it is formed in the reaction by adding acid to a pH of 6–8 and definitely below 10 when using preferred solvents. The reaction is conducted in the presence of a diluent or solvent such as water or an organic solvent. Although water can be used without admixture with one of the other solvents, it is usually preferred to admix the water with ethanol in approximately equal amounts for use as a solvent. The use of water as a solvent without admixture with ethanol requires a higher temperature and generally requires the use of elevated pressure. When using a water ethanol-solvent, the temperature of reaction is from 50°–120° C. If no ethanol is used the same temperature range can be employed, however a reaction time of 2–3 days will be required. If a reaction temperature of 190° C. is used without ethanol the reaction time will be 1 to 2 hours. With respect to times and temperatures of the specific examples, the first six specific examples utilizing water and ethanol as the cosolvents and a temperature 80°–83° C. were from 4¾ to 25 hours. In examples 7–9 only water was used and a pressure bomb was used as the reactor. A temperature range of 175° to 195° C. brought a reaction time of 1¾ to 2 hours. There is no mention of continuous processes in either reference and all the Gaertner examples are batch processes.

A new process for preparing alkoxylated alkyl glyceryl ether sulfonates has now been discovered. This process is continuous with a short reactor time and utilizes high contact quantities of sulfonated product together with the reactants, while achieving unusually high solids content of sulfonated product with accompanying low moisture levels. The reaction temperature is readily controllable at least in part because of the surprisingly low viscosity of the reactor contents at high solids content of sulfonated product, thereby also allowing for easy handling at all stages of the continuous process.

SUMMARY OF THE INVENTION

In accordance with the invention there is a continuous process for preparing alkoxylated alkyl glyceryl ether sulfonates which comprises reacting in the presence of water a mixture of an alkali metal sulfite and bisulfite with a mixture of alkoxylated glycidyl ethers comprising a major quantity of a

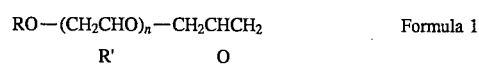

wherein R is alkyl or alkenyl of about eight to twenty carbon atoms, R' is H or methyl, n is an average value of 1 to about 12 to obtain alkoxylated sulfonated product having as a major quantity of the alkoxylated product

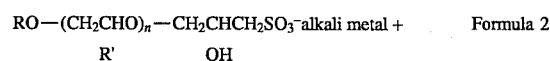

at an elevated temperature of at least 125° C., a pressure sufficient to maintain the reaction mass liquid at the reaction temperature and at least 20 wt % of the reaction mass as sulfonated product.

DETAILED DESCRIPTION OF THE INVENTION

Figure 1:
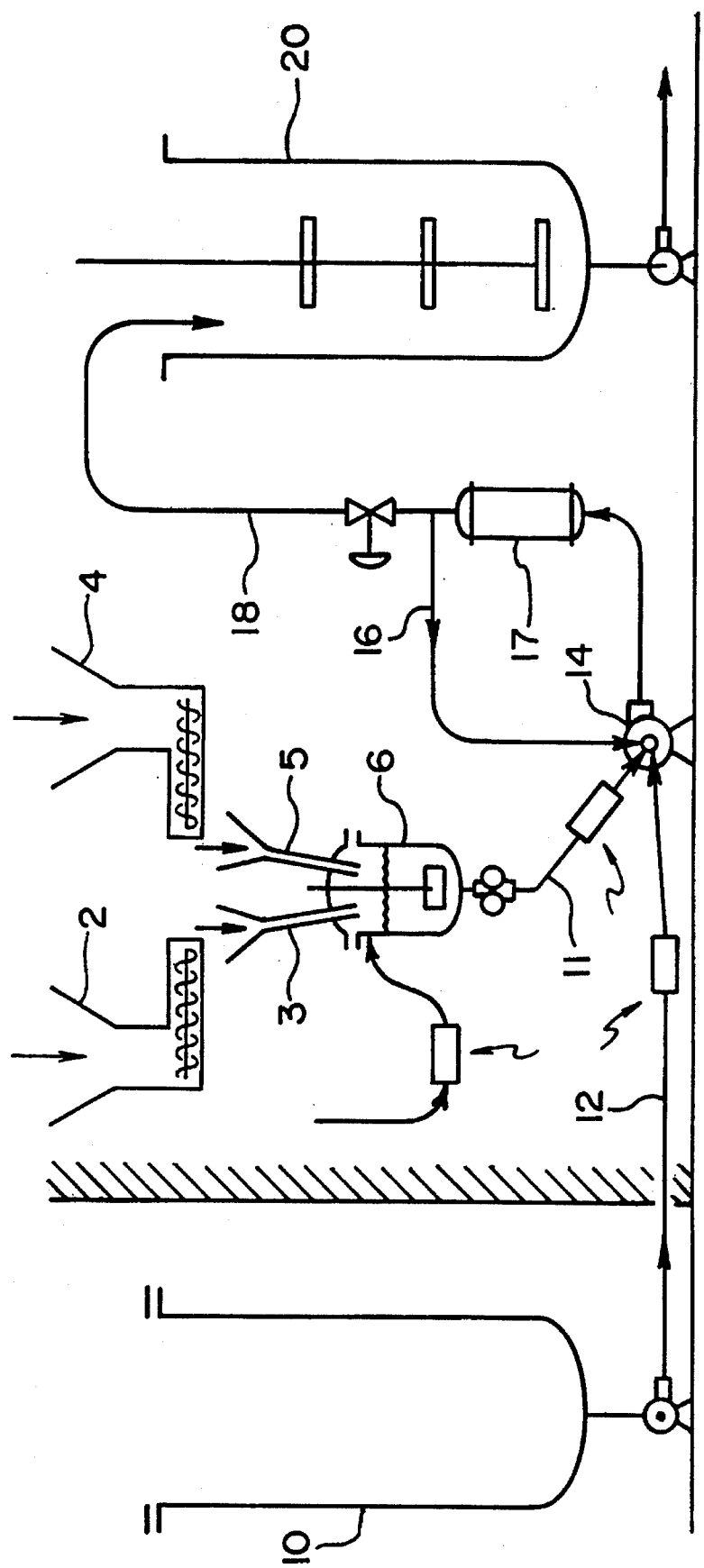

In the above formulae, R is preferably alkyl and more preferably normal alkyl although up to about 20 wt % of the R group can be branched alkyl. R has preferably about 12 to 18 carbon atoms, more preferably 12 to 15 carbon atoms. R' is preferably hydrogen. The variable n is preferably an average value of 1 to about 8 more preferably 1 to 3, or 1 or 2, most preferably 1. Illustrative of the alkali metals are sodium and potassium, preferably sodium.

The sulfite and bisulfite are present in weight ratio ranges in the reactor vessel to maximize the velocity and selectivity of the sulfonation reaction taking into account such factors as aqueous solubility, reaction rate of the alkoxylated glycidyl ether and any other glycidyl ether side reaction product as well as pH. Generally the sulfite should be in quantities of about 0.1 to about 35 wt % of the sulfite plus bisulfite, preferably about 15 to about 30 wt %. The sodium salt is preferred for the preparation of consumer products thereafter such as personal care compositions, oral care compositions, fabric care compositions and hard surface care compositions, particularly personal care compositions in liquid and solid form, preferably solid.

The temperature at which the continuous process takes place is generally at least 125° C. The temperature directly affects the rate of reaction and high temperatures can be employed as long as proper control of the exothermic reaction is maintained. Temperatures above about 140° C. are preferred. Although higher temperature can be employed, generally temperatures above about 200° C. are not preferred.

The major portion of the alkoxylated sulfonated product are the compounds of FIG. 2. However, there are present in the product minor portions of "dimer" alkoxylated sulfonated product derived from the diglycidyl ether shown below:

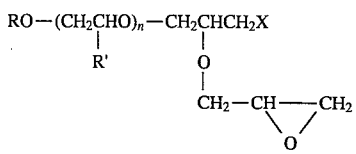

Formula 3 wherein R, R' and n are as previously defined and X is halo, preferably chloro, or hydroxy. This composition of Formula 3 is sulfonated as well and is part of the sulfonated product. Trimeric and small quantity of tetrameric glycidyl ether materials, similar to that shown in U.S. Pat. No. 3,024,273 can also be present and sulfonated. The chlorohydrin analogous materials are shown in U.S. Pat. No. 2,989,547. When n is a low average value, for example 1 to 2, a significant amount of the sulfonated product is not alkoxylated.

Pressure, in general, is not a significant reaction variable. The pressure should be sufficient to maintain the reaction mass as a liquid at the reaction temperature.

The presence of any solvent other than water, particularly an organic solvent such as ethanol is not preferred. Further purification steps would be necessary and that substance such as ethanol, could interfere with the end surfactant use, particularly as a lather depressant.

It has been found that the presence of significant quantities of sulfonated product in the reaction vessel is extremely beneficial to the reaction rate, (minimize induction period), the ease of handling and the economics of the process, particularly with respect to subsequent transporting of the reaction mass. Generally, the more concentrated in sulfonated product and the less moisture present, the more economic is the process and post process treatment steps. Therefore at least 20 wt % of the reaction mass in this continous process is at all times sulfonated product, even at the time the sulfite bisulfite mixture and glycidyl ether are first contacted within the reactor. It is understood that the glycidyl ether will also generally have small quantities of the diglycidyl ether, trimer and/or tetramer previously alluded to in the specification present together with the glycidyl ether of Formula 1. The reaction can generally be done in a continuous reactor but can also be done through a simple recycle loop as shown in U.S. Pat. No. 3,024,273. It is preferred to have at least about 40 wt % preferably at least about 50 wt % of the reaction mass being sulfonated product. The maximum amount of sulfonated product in the reaction mass is not unduly significant and is at least somewhat dependent upon the equilibrium point of the reaction and the workability, processability, of the reaction mass. It has been surprisingly found that very high solids content of sulfonated product in water can be achieved. The viscosity value surprisingly levels off or goes down at a certain sulfonated product content. For example, when n equals an average value 1, that certain sulfonated product content is about 50%. The term sulfonated product refers to any molecule which is sulfonated and thereby includes the sulfonated glycidyl ether of FIG. 3, the sulfonated "dimer" previously alluded to above as well as the small quantities of trimer and tetramer present. It also includes the sulfonated material wherein there are no alkoxy groups. Although the maximum point wherein viscosity of the reaction mass will significantly increase once more can vary, generally a quantity of sulfonated product of about 73–75 wt %, preferably about 70 wt % or above 65 wt % is where the viscosity can begin to significantly rise above the point where it began to fall or level off. A preferred range is above 50 to about 70 wt % of sulfonated product. Such a high solid content but still workable reaction mass provides major advantage in handling, cost savings in transport, and processing the sulfonated product into cleansing composition, particularly personal care cleansing composition. Processability (stirrability) of the reaction mass and proper control of the exothermic reaction is readily maintained.

The amount of water in the reactor vessel is at least somewhat dependent upon the quantity of sulfonated product therein. It has been found that the quantity of water can be brought down to very low levels, far lower than could have been predictable and still maintain an easily workable, processable reaction mass in properly designed equipment. Levels of water of 28% or lower can be maintained, preferably 25% or lower. The minimum level of water is that which still allows for good processing and working of the reaction mass. Generally, levels of water below 12 wt % provide a difficultly workable reaction mass. It is preferred to maintain levels of moisture above about 14 wt %.

The reaction can reach completion in the reactor if given sufficient resident time or preferably removed from the reactor vessel after achieving a level substantially near completion such as 40–90% conversion of glycidyl ether, and then transferred to a storage vessel at atmospheric pressure wherein the reaction goes to completion in the storage vessel up to about 6 hours at temperatures of about 90° to 110° C.

The process will now be explained with reference to the drawing attached to and part of the specification as designated as FIG. I, an illustration of the continuous process of this invention. Any numbers present in the process flow Figure are exemplary of the process and are not meant to unduly limit the process.

With reference to the Figure, sodium metabisulfite from storage container 2 and sodium sulfite from storage container 4 are metered into solution tank, 6, using lines 3 and 5 respectively and mixed with water metered through line 1 into solution tank 6, wherein a solution/suspension of sulfite bisulfite mixture is prepared. Glyceryl epoxide stored in tank 10 is metered through line 12 to the recycle pump, 14, wherein it enters into the recycling stream in the recycle loop, 16, having a heat exchanger, 17, simultaneously with the aqueous solution/suspension of the mixture of bisulfite sulfite metered through line 11. The recycling reaction mass is maintained a temperature of 160° C. and at a pressure of 160 psig. The holdup volume of the recycle loop is chosen so that there is at least 20 wt % sulfonated product (A.I.) present at all times in the recycling stream, preferably at least about 40 wt % sulfonated product, still more preferably at least about 50 wt %.

As an example, when the hold up time is 5 minutes, the product exiting the recycle loop through 18 contains approximately 40–62% A.I. The reaction is completed in the product storage tank 20, wherein the temperature is maintained at 104° C., i.e., the equilibrium temperature at which the product flashes into the atmosphere.

The following are examples of the specific process and results which can be acheived therefrom.

EXAMPLE 1

An aqueous solution of sodium sulfite and bisulfite was prepared by mixing 38.8 lbs of sodium metabisulfite and 17.0 lbs of sodium sulfite with 88.2 lbs of water. The salt solution was metered into the recycle loop at a rate of 7.6 lbs per hour. Simultaneously a glyceryl epoxide wherein R is normal alkyl of 12 to 15 carbon atoms, R' is hydrogen and n is average value of 1 according to Formula 1 was metered into the recycle loop at a rate of 10.0 lbs/hour. The recycle loops residence time was thirty minutes. At steady state, the temperature maintained in the recycle loop was 160° C. and the pressure was 100 psig. The residence times were varied in sequential runs by increasing the metering rates of the reactants proportionately to achieve residence times of 15, 10 and 5 minutes.

Analytical Results:

| Residence Time | % AI | % H2O |
| --- | --- | --- |
| 30 min | 64.1 | 19.5 |
| 15 Min | 64.1 | 20.1 |
| 10 Min | 63.0 | 18.9 |
| 5 Min | 65.0 | 16.8 |

The above numbers were achieved after the reaction mass was flashed into a holding tank. At five minute residence time, the reactor composition had a % A.I. of 52.2 wt % and a % water of 24.5 wt %.

At all times the reaction mass was readily pumpable.

EXAMPLE 2

Following in general the procedure of example 1 but using a salt solution made from 120 lbs of water, 43.5 lbs of sodium metabisulfite and 19.5 lbs of sodium sulfite, this solution was metered into the recycle loop at a rate of 16.5 lbs/hr. Simultaneously, the glyceryl epoxide of Example 1 was metered into the recycle loop at a rate of 19.5 lbs/hr. Temperature and pressure were maintained as in Example 1. The residence time was 15 minutes. The metering rates were than adjusted to provide residence time of 10 and 5 minutes. The product leaving the recycle loop flashed to atmospheric pressure and after flashing reached an equilibrium temperature of 104° C. and was maintained at 104° C. for 6 hours.

Below are the A.I. (sulfonated product) achieved for each recycle loop residence time as well as the wt % water attained at the end of the 6 hour storage period.

% AI vs Incubation Time for each Reactor Residence time

| Incubation Time at 104° C. (hrs.) | Reactor Residence Time (minutes) | | |
| --- | --- | --- | --- |
| | 5 | 10 | 15 |
| 0.00 | 61.9 | 59.5 | 59.6 |
| 0.25 | — | 60.0 | 61.0 |
| 0.77 | — | — | 61.1 |
| 1.00 | 62.0 | 61.5 | 61.4 |
| 2.00 | 62.8 | 62.0 | 62.5 |
| 3.00 | 63.2 | 63.6 | 63.0 |
| 6.00 | 65.8 | 64.1 | 64.7 |

Wt % H₂O at Residence time plus 6 hours incubation time

| Residence Time | wt % H$_2$O |
| --- | --- |
| 5 min | 22.2 |
| 10 min | 22.0 |
| 15 min | 22.1 |

The actual composition within the reactor prior to flashing had the following analytical data.

| Residence Time | wt % A.I. | wt % H$_2$O |
| --- | --- | --- |
| 5 min | 58.0 | 27.1 |
| 10 min | 55.8 | 26.9 |
| 15 min | 55.9 | 27.0 |

I claim:

1. A continuous process for preparing alkoxylated alkyl glyceryl ether sulfonates which comprises reacting in a reactor in the presence of water, a mixture of an alkali metal sulfite and bisulfite with a mixture of alkoxylated glycidyl ethers comprising a major quantity of $$\text{RO}-(\text{CH}_2\text{CHO})_n-\text{CH}_2\text{CHCH}_2 \atop \text{R'} \quad\quad \text{O}$$

wherein R is alkyl or alkenyl of about eight to twenty carbon atoms, R' is H, n is an average value of 1 to 3 to obtain alkoxylated sulfonated product comprising a major quantity of $$\text{RO}-(\text{CH}_2\text{CHO})_n-\text{CH}_2\text{CHCH}_2\text{SO}_3\text{-alkali metal}+ \atop \text{R'} \quad\quad \text{OH}$$

at an elevated temperature of at least 125° C., a pressure sufficient to maintain the reaction mass liquid at the reaction temperature and at least 40 wt % of the reaction mass is sulfonated product, wherein prior to reaction completion the reaction mass is withdrawn from the reactor and transferred to a storage vessel where the reaction is allowed to go to completion.

2. The process in accordance with claim 1 wherein the temperature is at least about 140° C., n is an average value of 1 and sulfonated product is at least about 50 wt %.

3. The process in accordance with claim 2 wherein the alkyl group R is normal alkyl of twelve to fifteen carbon atoms and water in the reaction mass is no greater than 28 wt %.

4. The process in accordance with claim 3 wherein up to about 20 wt % of the R group is branched, the remainder being normal, and at least 12 wt % of the reaction mass is moisture.

5. The process in accordance with claim 1 wherein sulfonated product is further processed into a personal cleansing composition.

6. The process in accordance with claim 5 wherein n is an average value of 1, R is normal alkyl and the cleansing composition is a bar.

7. The process in accordance with claim 1 wherein the alkali metal is sodium.

8. The process in accordance with claim 1 wherein the storage vessel is at atmospheric pressure.

9. The process in accordance with claim 8 wherein the reaction mass is transferred to the storage vessel when 40 to 90% of the said glycidyl ether is converted.

10. A continuous process for preparing alkoxylated alkyl glyceryl ether sulfonates which comprises reacting in the presence of water, a mixture of an alkali metal sulfite and bisulfite with a mixture of alkoxylated glycidyl ethers comprising a major quantity of a $$RO-(CH_2CHO)_n-CH_2CHCH_2$$
$$\phantom{RO-(CH_2C}|\phantom{HO)_n-CH_2}\diagdown\!\diagup$$
$$\phantom{RO-(CH_2C}R'\phantom{HO)_n-CH_2C}O$$

wherein R is alkyl or alkenyl of about eight to twenty carbon atoms, R' is H or methyl, n is an average value of 1 to 3 to obtain alkoxylated sulfonated product comprising a major quantity of $$RO-(CH_2CHO)_n-CH_2CHCH_2SO_3\text{-alkali metal +}$$
$$\phantom{RO-(CH_2C}|\phantom{HO)_n-CH_2C}|$$
$$\phantom{RO-(CH_2C}R'\phantom{HO)_n-CH_2}OH$$

at an elevated temperature of at least 125° C. to about 200° C., a pressure sufficient to maintain the reaction mass liquid at the reaction temperature, a residence time of about 5 to about 30 minutes, and at least 20 wt % of the reaction mass is sulfonated product.

11. The process in accordance with claim 10 wherein the alkali metal is sodium.

12. The process in accordance with claim 10 wherein R' is hydrogen and n is an average value of 1.

13. The process in accordance with claim 12 wherein the sulfonated product is from about 50 to 75 wt % of the reaction mass.

14. The process in accordance with claim 13 wherein the water in the reaction mass is 25 wt % or lower.

15. The process in accordance with claim 12 wherein the temperature is from about 140° C. to about 200° C.

16. The process in accordance with claim 12 wherein the process is carried out in the essential absence of an organic solvent.

17. The process in accordance with claim 16 wherein the organic solvent is ethanol.

18. The process in accordance with claim 17 wherein the sulfonated product is about 50 to 70 wt % of the reaction mass and the water is less than about 25 wt % of the reaction mass.

* * * * *